US010133998B2

(12) United States Patent
Dill

(10) Patent No.: US 10,133,998 B2
(45) Date of Patent: Nov. 20, 2018

(54) SYSTEM AND METHODS FOR THE SELECTION, MONITORING AND COMPENSATION OF MENTORS FOR AT-RISK PEOPLE

(71) Applicant: David A. Dill, Newtown, PA (US)

(72) Inventor: David A. Dill, Newtown, PA (US)

( * ) Notice: Subject to any disclaimer, the term of this patent is extended or adjusted under 35 U.S.C. 154(b) by 0 days.

(21) Appl. No.: 15/623,206

(22) Filed: Jun. 14, 2017

(65) Prior Publication Data

US 2018/0075381 A1    Mar. 15, 2018

Related U.S. Application Data

(63) Continuation-in-part of application No. 15/373,869, filed on Dec. 9, 2016, now Pat. No. 10,068,194, which is a continuation-in-part of application No. 15/266,384, filed on Sep. 15, 2016, and a continuation-in-part of application No. 15/337,799, filed on Oct. 28, 2016, now Pat. No. 10,019,688, which is a continuation of application No. 15/266,384.

(51) Int. Cl.
G06Q 10/06    (2012.01)
G06Q 30/02    (2012.01)

(52) U.S. Cl.
CPC ..... *G06Q 10/0635* (2013.01); *G06Q 30/0208* (2013.01)

(58) Field of Classification Search
None
See application file for complete search history.

(56) References Cited

U.S. PATENT DOCUMENTS

| 6,470,319 | B1* | 10/2002 | Ryan | G06Q 10/10 |
| | | | | 705/325 |
| 8,472,862 | B2 | 6/2013 | Yaskin et al. | |
| 9,416,420 | B2* | 8/2016 | Faham | C12Q 1/6883 |
| 2003/0037063 | A1* | 2/2003 | Schwartz | G06Q 40/08 |
| 2003/0088434 | A1* | 5/2003 | Blechman | G06Q 10/10 |
| | | | | 705/2 |
| 2003/0233278 | A1* | 12/2003 | Marshall | G06Q 30/00 |
| | | | | 705/14.35 |
| 2004/0267569 | A1 | 12/2004 | Camp | |
| 2006/0155558 | A1 | 7/2006 | Corpening | |

(Continued)

OTHER PUBLICATIONS

U.S. Appl. No. 15/373,869, filed Dec. 9, 2016, Pending.

(Continued)

*Primary Examiner* — Thomas L Mansfield
(74) *Attorney, Agent, or Firm* — Ping Wang; Morris, Manning & Martin, LLP

(57) ABSTRACT

A method for providing incentive to mentors of at-risk mentees is described. The method includes the steps of determining an at-risk mentee's prospects in the absence of mentoring, and then tracking behavior and progress in a period of time, determining the mentee's achievement of important milestones, avoidance of costs to society, and/or income and income tax payments during the same period of time, and calculating a financial incentive to the mentee's mentor, wherein the amount of the financial incentive is calculated based on the mentee's behavior, achievement of important milestones, avoidance of costs to society, and/or income tax payments during the period of time.

20 Claims, 3 Drawing Sheets

(56) References Cited

U.S. PATENT DOCUMENTS

| | | | |
|---|---|---|---|
| 2007/0094039 A1* | 4/2007 | Grant | G06Q 10/00 |
| | | | 705/1.1 |
| 2007/0122780 A1 | 5/2007 | Moon et al. | |
| 2008/0071578 A1* | 3/2008 | Herz | G06Q 10/0635 |
| | | | 705/3 |
| 2010/0120011 A1 | 5/2010 | O'Brien | |
| 2012/0117188 A1 | 5/2012 | Nidiffer et al. | |
| 2012/0221485 A1* | 8/2012 | Leidner | G06Q 10/0635 |
| | | | 705/36 R |
| 2012/0221486 A1* | 8/2012 | Leidner | G06Q 10/0635 |
| | | | 705/36 R |
| 2012/0282576 A1 | 11/2012 | Chenoweth et al. | |
| 2013/0138397 A1 | 5/2013 | Kiet | |
| 2013/0318005 A1 | 11/2013 | Bass et al. | |
| 2014/0032291 A1 | 1/2014 | Sheperd | |
| 2014/0278730 A1* | 9/2014 | Muhart | G06Q 10/0635 |
| | | | 705/7.28 |
| 2015/0006259 A1 | 1/2015 | Yoo | |
| 2015/0324467 A1 | 11/2015 | Belton, Jr. et al. | |
| 2016/0092906 A1 | 3/2016 | Cioffi | |
| 2016/0098530 A1 | 4/2016 | Dill et al. | |

OTHER PUBLICATIONS

U.S. Appl. No. 15/337,799, filed Oct. 28, 2016, Pending.
U.S. Appl. No. 15/266,384, filed Sep. 15, 2016, Pending.
U.S. Appl. No. 15/621,881, filed Jun. 14, 2017.
International Search Report and the Written Opinion of the International Searching Authority of Application No. PCT/US2017/049418 dated Nov. 13, 2017.

* cited by examiner

SYSTEM AND METHODS FOR THE SELECTION, MONITORING AND COMPENSATION OF MENTORS FOR AT-RISK PEOPLE

This application is a Continuation-In-Part of U.S. application Ser. No. 15/373,869, filed on Dec. 9, 2016, which is a Continuation-In-Part of U.S. application Ser. No. 15/266,384, filed on Sep. 15, 2016. This application also claims priority from application Ser. No. 15/337,799, filed on Oct. 28, 2016, which is a Continuation of U.S. application Ser. No. 15/266,384, filed on Sep. 15, 2016. The entirety of the aforementioned applications is incorporated herein by reference.

FIELD

This disclosure is generally related to systems and methods for mentoring at-risk people. In particular, this disclosure is related to systems and methods for improving matching between mentors and mentees, improving the success of relationships between mentors and mentees, and for providing incentives to mentors.

BACKGROUND

Even though current mentoring systems operate on a very small scale for a short period of time, the mentoring systems provide a substantial impact on, for example, children from troubled backgrounds and people who have recently been released from prison. However, in the current mentoring systems, no quantitative method exists for pairing a potential mentee with a potential mentor with a view to maximizing a probability of a successful mentor-mentee relationship on a long term basis. Additionally, in current mentorship systems, the mentor is not financially compensated for being a successful mentor and has little ongoing incentive to establish a long term supportive relationship with the mentee. Moreover, there are many more people who need mentors than can be satisfied by the current mentor volunteers.

Accordingly, there is a need for systems and methods for improving the pairing between mentors and mentees. There is also a need for systems and methods for financially compensating successful mentors on a long term basis in order to greatly increase the supply of mentors.

SUMMARY

One aspect of the present application relates to a method for providing mentoring service to at-risk people, comprising the steps of: receiving, via a user interface of an application executing on one or more computer processors, a personal profile concerning an at-risk subject, wherein the personal profile comprises personal data, a risk profile comprises a plurality of risk factors and a plurality of mentee matching tags; assigning, via the one or more computer processors, a risk point value to each of the plurality of risk factors based on severity level of the subject's risk factors and a risk point matrix stored on a memory device accessible by the one or more computer processors, wherein the risk point matrix is determined by evaluating a large scale database reflecting risks of other subjects compared to their later successes or failures, and estimated lifetime costs to society; determining, via the one or more computer processors, a total risk point value of the at-risk subject via the one or more computer processors; accepting the at-risk subject as a mentee candidate, if the total risk point value satisfies a pre-determined threshold value; searching, via the one or more computer processors, a mentor candidate database comprising a plurality of mentor profiles, wherein each mentor profile comprises personal data, mentoring experience and a plurality of mentor matching tags; assigning, via the one or more computer processors, at least one mentor candidate to the mentee candidate, wherein the at least one mentor candidate is selected based on a match between the mentee matching tags and the mentor matching tags, where in the match is performed using a matching algorithm; submitting the at least one assigned mentor candidate to an oversight board for approval; receiving, via the user interface of the application, the at-risk subject's progress report after the establishment of a mentor-mentee relationship; comparing, via the one or more computer processors, the at-risk subject's progress to at-risk individual's success odds or ex-convict success odds stored on a memory device accessible by the one or more computer processors; obtaining, via the one or more computer processors, (1) the at-risk subject's income tax records from relevant governmental agencies, (2) the at-risk subject's retirement plan (e.g., 401(k)) contribution information, and/or education plan (e.g., the 529 plan) contribution information from relevant financial institutions; determining, via the one or more computer processors, a financial incentive to the mentor based on result of the comparing step, the at-risk subject's income tax records, the at-risk subject's retirement plan contribution information and/or education plan contribution information, and expected lifetime costs to society; obtaining approval for the amount of financial incentive from the oversight board; and transmitting a notice to the relevant governmental agency about the approved amount.

Another aspect of the present application relates to a system for providing mentoring service to at-risk people, comprising: one or more computer processors; and one or more tangible, non-transitory computer readable media accessible by the one or more computer processors, wherein the one or more tangible, non-transitory computer readable media comprise instructions that, when executed by the one or more processors, cause the one or more processors to perform: receiving, via a user interface of an application executing on the one or more computer processors, a risk profile concerning an at-risk subject, wherein the risk profile comprises a plurality of risk factors and their expected lifetime costs to society; assigning, via the one or more computer processors, a risk point value to each of the plurality of risk factors based on severity level of the subject's risk factors and their expected lifetime cost to society and a risk point matrix stored on a memory device accessible by the one or more computer processors, wherein the risk point matrix is determined by evaluating a large scale data base reflecting risks of other subjects compared to their later successes or failures and expected lifetime costs to society; determining, via the one or more computer processors, a total risk point value of the at-risk subject via the one or more computer processors; accepting the at-risk subject as a mentee candidate, if the total risk point value satisfies a pre-determined threshold value; searching, via the one or more computer processors, a mentor candidate database comprising a plurality of mentor profiles, wherein each mentor profile comprises personal data, mentoring experience and a plurality of mentor matching tags; assigning, via the one or more computer processors, at least one mentor candidate to the mentee candidate, wherein the at least one mentor candidate is selected based on a match between the mentee matching tags and the mentor matching tags, where in the match is performed using a matching algorithm;

submitting the at least one assigned mentor candidate to an oversight board for approval; receiving, via the user interface of the application, the at-risk subject's progress report after the establishment of a mentor-mentee relationship; comparing, via the one or more computer processors, the at-risk subject's progress to the progress achieved by other at-risk individuals and their success odds or ex-convict progress and success odds stored on a memory device accessible by the one or more computer processors; obtaining, via the one or more computer processors, (1) the at-risk subject's income tax records from relevant governmental agencies, and/or (2) the at-risk subject's retirement plan contribution information, and/or education plan contribution information from relevant financial institutions; determining, via the one or more computer processors, a financial incentive to the mentor based on result of the comparing step, the at-risk subject's income tax records, the at-risk subject's retirement plan contribution information and/or education plan contribution information, and expected lifetime costs to society; obtaining approval for the amount of financial incentive from the oversight board; and transmitting a notice to the relevant governmental agency about the approved amount.

Another aspect of the present application relates to a tangible, non-transitory computer readable medium, comprising instructions that, when executed by a computer processor, cause the processor to perform: receiving, via a user interface on a computer, a risk profile concerning an at-risk subject, wherein the risk profile comprises a plurality of risk factors; assigning, via a computer processor, a risk point value to each of the plurality of risk factors based on severity level of the subject's risk factors and a risk point matrix stored on a memory device accessible by the computer processor, wherein the risk point matrix is determined by evaluating a large scale data base reflecting risks of other subjects compared to their later successes or failures and estimated lifetime cost to society; determining, via the computer processor, a total risk point value of the at-risk subject via the one or more computer processors; accepting the at-risk subject as a mentee candidate, if the total risk point value satisfies a pre-determined threshold value; searching, via the computer processor, a mentor candidate database comprising a plurality of mentor profiles, wherein each mentor profile comprises personal data, mentoring experience and a plurality of mentor matching tags; assigning, via the computer processor, at least one mentor candidate to the mentee candidate, wherein the at least one mentor candidate is selected based on a match between the mentee matching tags and the mentor matching tags, where in the match is performed using a matching algorithm; submitting the at least one assigned mentor candidate to an oversight board for approval; receiving, via the user interface of the application, the at-risk subject's progress report after the establishment of a mentor-mentee relationship; comparing, via the computer processor, the at-risk subject's progress to at-risk individual success odds or ex-convict success odds stored on a memory device accessible by the computer processor; obtaining, via the computer processor, (1) the at-risk subject's income tax records from relevant governmental agencies, and/or (2) the at-risk subject's retirement plan contribution information, and/or education plan contribution information from relevant financial institutions, and/or (3) the at-risk subject's criminal and prison records and their related costs, and/or (4) the amounts received by the at-risk subject from welfare and/or food stamp payments; determining, via the one or more computer processors, a financial incentive to the mentor based on result of the comparing step, the at-risk subject's income tax records, the at-risk subject's retirement plan contribution information and/or education plan contribution information, and expected lifetime costs to society from criminal activity, prison costs, court costs, welfare payments, food stamp payments, and similar costs to society; determining, via the computer processor, a financial incentive to the mentor based on result of the comparing step and the at-risk subject's income tax records and estimated lifetime costs to society; obtaining approval for the amount of financial incentive from the oversight board; and transmitting a notice to the relevant governmental agencies about the approved amount, wherein the financial incentive is provided in the form of a cash payment to the mentor, wherein amount of the cash payment is calculated as a percentage of the at-risk subject's income tax payment, the at-risk subject's retirement plan contribution information and/or education plan contribution each year or reflects payment based on the mentee's achievement of one or more milestones or avoidance of events that results in costs to society and wherein said notice causes the relevant governmental agency to issue a payment for the approved amount.

BRIEF DESCRIPTION OF THE DRAWINGS

The present application can be better understood by reference to the following drawings, wherein like references numerals represent like elements. The drawings are merely exemplary to illustrate certain features that may be used singularly or in any combination with other features and the present invention should not be limited to the embodiments shown.

DETAILED DESCRIPTION

Figure 1:
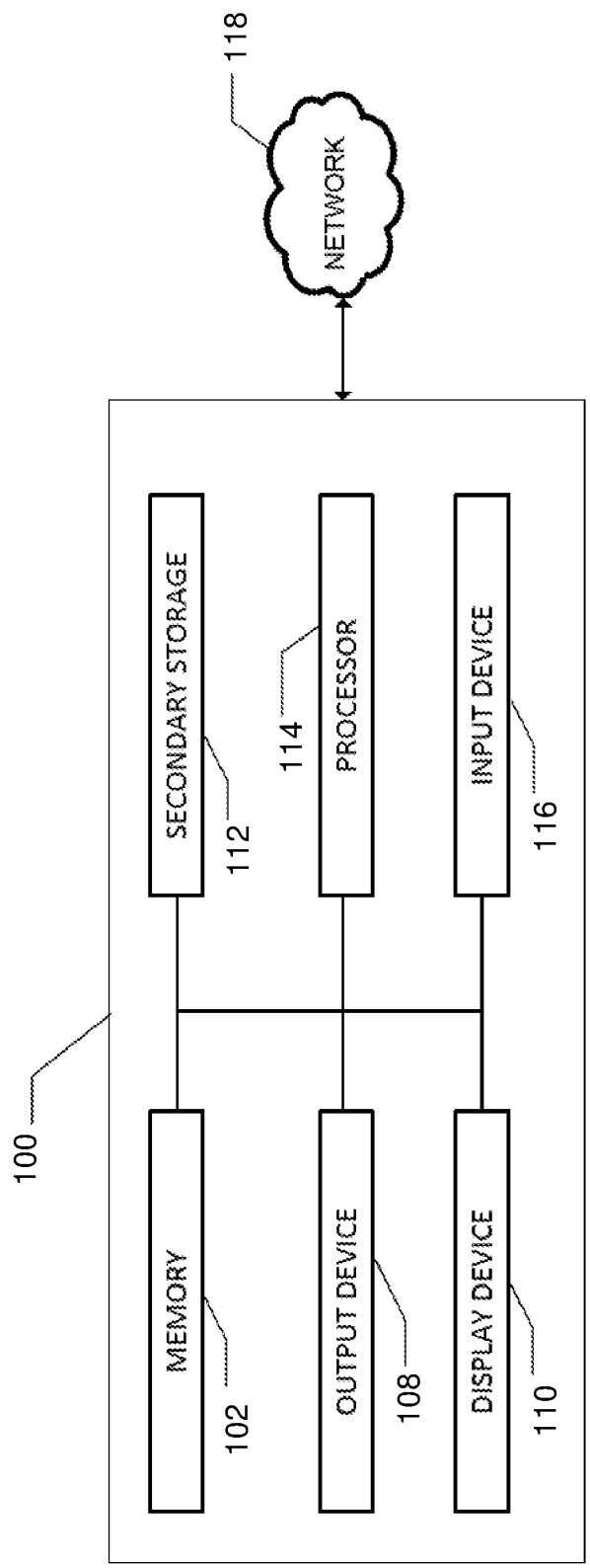
FIG. 1 shows an embodiment of the system of present application

The following detailed description is presented to enable any person skilled in the art to make and use the object of this application. For purposes of explanation, specific nomenclature is set forth to provide a thorough understanding of the present application. However, it will be apparent to one skilled in the art that these specific details are not required to practice the subject of this application. Descriptions of specific applications are provided only as representative examples. The present application is not intended to be limited to the embodiments shown, but is to be accorded the widest possible scope consistent with the principles and features disclosed herein.

This description is intended to be read in connection with the accompanying drawings, which are to be considered part of the entire written description of this application. The drawing figures are not necessarily to scale and certain features of the application may be shown exaggerated in scale or in somewhat schematic form in the interest of clarity and conciseness.

As used herein, the term "at-risk" refers to individuals, groups, populations or sub-populations who are considered to have a higher probability of failing socially, economically, academically or morally. The term may be applied to those who face circumstances that could jeopardize their ability to complete school, get or retain employment, or avoid criminal activity. Such people may have higher than average rates of homelessness, poverty, incarceration, teenage pregnancy, serious health issues, domestic violence, transiency, gang activity, drug use, or other criminal activity or conditions. Such people may also have learning disabilities, low test scores, disciplinary problems, grade retentions, or other learning-related factors that have adverse effects.

As used herein, "recidivism" refers to repeated or habitual relapse into a behavior such as crime, or the chronic tendency toward repetition of criminal or antisocial behavior patterns.

As used herein, the term "mentee" refers to an at-risk individual who agrees to accept the instruction, guidance, support and encouragement of an individual tasked with aiding the mentee become a successful member of society.

As used herein, the term "mentor" refers to an individual who provides instruction, guidance, support and encouragement to a mentee for the purpose of aiding the mentee to become a successful member of society.

As used herein, the term "wireless" means any wireless signal, data, communication, or other interface including without limitation Wi-Fi, Bluetooth, 3G, HSDPA/HSUPA, TDMA, CDMA (e.g., IS-95A, WCDMA, etc.), FHSS, DSSS, GSM, PAN/802.15, Wi-MAX (802.16), 802.20, narrowband/FDMA, OFDM, PCS/DCS, analog cellular, CDPD, satellite systems, millimeter wave or microwave systems, acoustic, and infrared (i.e., IrDA).

As used herein, the terms "Internet" and "internet" are used interchangeably to refer to inter-networks including, without limitation, the Internet.

As used herein, the term "memory" includes any type of integrated circuit or other storage device adapted for storing digital data including, without limitation, ROM. PROM, EEPROM, DRAM, SDRAM, DDR/2 SDRAM, EDO/FPMS, RLDRAM, SRAM, "flash" memory (e.g., NAND/NOR), and PSRAM.

As used herein, the term "computer processor" refers generally to all types of digital processing devices including, without limitation, digital signal processors (DSPs), reduced instruction set computers (RISC), general-purpose (CISC) processors, microprocessors, gate arrays (e.g., FPGAs), PLDs, reconfigurable compute fabrics (RCFs), array processors, and application-specific integrated circuits (ASICs). Such digital processors may be contained on a single unitary IC die, or distributed across multiple components.

As used herein, the term "at-risk subject's income tax records" include the at-risk subject's federal, state and/or city income tax records, and, in some embodiments, also include the at-risk subject's family's federal, state and/or city income tax records.

As unused herein, the term "costs to society" include costs of welfare, food stamps, unemployment payments, Medicaid, teenage pregnancy, drug use, crime, prison, lack of income tax payments, failing to graduate from high school, etc. The term "lifetime costs to society" include lifetime costs of welfare, food stamps, unemployment payments, Medicaid, teenage pregnancy, drug use, crime, prison, lack of income tax payments, failing to graduate from high school, etc.

One basic premise that lies behind the present disclosure is that "success breeds success." Individuals who have exposure to, and guidance from, persons who are successful have a greater chance of becoming successful themselves. Individuals who lack successful role models in their lives experience a greater likelihood of failure or recidivism. Accordingly, the present application seeks to link at-risk children and adults (referred to together as "at-risk individuals") with mentors who will have a lifelong economic motivation to ensure their success. The mentors would be compensated based on the future success of their mentees, such as with some fraction of the income tax payments by their mentees or some other metric reflective of their success as productive citizens. In this manner, the mentors will have a strong ongoing multi-year motivation to advise, coach, implore, train, and otherwise influence the success of their mentees. They would want them to get educated, avoid crime and drug use, and would even be motivated to help them get good jobs. They would be interested in maximizing their long-term success. They may share their wisdom, or offer them jobs, or recommend them for certain positions or opportunities. Their friends and relatives may also be motivated to help the mentee since it would be beneficial to the mentor. The same principles can be applied to prisoners who have served their time. For such mentors, the economic incentive could be based on income tax payments by their mentees over some extended number of years or it could also include a bonus for reaching certain milestones (such as high school graduation, college attendance, college graduation, avoidance of future crime, avoidance of future jail time, etc.) or for each day or week or month or year of crime free activity by their mentees and their avoidance of costs to society.

Based on the success of various social and charity programs that lack any type of long term economic incentive, applicant has come to the conclusion that a properly constructed large scale effort could radically improve the success rate of at-risk people of all ages, while improving race relations and reducing crime, welfare expenses (and other costs to society), and reducing the national debt by trillions of dollars.

Method for Providing Mentoring Service to at-Risk People

One aspect of the present application relates to a method for providing mentoring service to at-risk people. The method comprises the steps of: receiving, via a user interface of an application executing on one or more computer processors, a risk profile concerning an at-risk subject, wherein the risk profile comprises a plurality of risk factors; assigning, via one or more computer processors, a risk point value to each of the plurality of risk factors based on severity level of the subject's risk factors and a risk point matrix stored on a memory device accessible by the one or more computer processors; determining, via the application, a total risk point value of the subject via the one or more computer processors; and when the total risk point value reaches a predetermined threshold value, accepting the at-risk subject as a mentee candidate. In some embodiments, a higher severity level of a risk is assigned a higher risk point. The total risk point value reaches the predetermined threshold value if the total risk point value equals to or exceeds the threshold value. In other embodiments, a higher severity level of a risk is assigned a lower risk point. The total risk point value reaches the predetermined threshold value if the total risk point value equals to or below the threshold value.

Examples of the risk factors include, but are not limited to, age, gender, weight, height, job history, history of traffic violations, alcohol consumption, drug use history, personal medical history, academic performance in school, attendance history at school, appropriateness of behavior at school (such as avoiding fighting, bullying, cheating or other disruptive behavior), extra-curricular activities, gang involvement, personality assessment, assessment of siblings and/or parents and/or guardians, probability of dropping out of school, probability of becoming pregnant, probability of committing a crime, probability of using illegal drugs, job history, probability of becoming habitually unemployed, probability of returning to prison, and other risk factors.

In some embodiments, the risk point matrix is determined by evaluating a large scale data base reflecting risks of other subjects compared to their later successes or failures and estimated lifetime cost to society.

As used herein, the term "user interface of an application" refers to, without limitation, any visual, graphical, tactile, audible, sensory, digital or other means of providing information to and/or receiving information from a user or other entity. A user interface of an application includes means for receiving information from a tangible storage media, such as a flash drive, or from internet.

In some embodiments, the method further comprises the steps of: assigning, via the one or more computer processors, a mentor candidate to the at-risk subject, wherein the mentor is selected from a mentor qualification database on a memory device accessible by the one or more computer processors; and approving the assigned mentor by an oversight board. In some embodiments, the oversight board may include at least one member from local community, at least one member with juvenile correction experience and/or at least one member from the criminal justice system. In some embodiments, the oversight board also includes a representative from a local, state or federal government. In some embodiments, the oversight board includes a representative from a tax agency of the local, state or federal government.

In some embodiments, the method further comprises the steps of searching, via the one or more computer processors, a mentor candidate database comprising a plurality of mentor profiles, wherein each mentor profile comprises personal data, mentoring experience and a plurality of mentor matching tags; and assigning, via the one or more computer processors, at least one mentor candidate to the mentee candidate, wherein the at least one mentor candidate is selected based on a match between the mentee matching tags and the mentor matching tags, where in the match is performed using a matching algorithm.

In some embodiments, the method further comprises the steps of receiving, via the user interface of the application, the at-risk subject's progress report after the establishment of a mentor-mentee relationship; and comparing, via the one or more computer processors, the at-risk subject's progress to the progress achieved by other at-risk individuals and their success odds or ex-convict progress and success odds stored on a memory device accessible by the one or more computer processors.

In some embodiments, the method further comprises the steps of: retrieving, via the one or more computer processors, information about how to reduce risks associated with one or more of the plurality of risk factors from a database stored on a memory device, and electronically delivering, via the one or more computer processors, the information to the oversight board and/or a mentor approved by the oversight board and/or parents or guardians of the mentee. In some embodiments, the information is delivered over a wireless communication channel to a wireless device associated with the mentor.

In some other embodiments, the method further comprises the steps of: retrieving, via the one or more computer processors, information about how to reduce risks associated with one or more of the plurality of risk factors from a database stored on a memory device, and electronically delivering, via the one or more computer processors, an alert to the mentor (or other appropriate interested parties) over a wireless communication channel to a wireless device associated with the mentor, wherein the alert activates an application on the wireless device that causes the wireless device to connect, via Internet, to the one or more computer processors and download said information.

In some embodiments, the method further comprises the steps of: receiving, via a user interface of the application, the at-risk subject's progress report after the establishment of a mentor-mentee relationship; comparing, via one or more computer processors, the at-risk subject's progress to at-risk individual success odds or ex-convict success odds stored on a memory device accessible by the one or more computer processors; providing, via the one or more computer processors, a financial incentive to the mentor based on result of the comparing step; and maintaining, via the one or more computer processors, a mentor incentive database, wherein the mentor incentive database is stored on a tangible medium accessible by the one or more computer processors. In some embodiments, the financial incentive calculation is subject to review by an oversight board so that, if necessary, adjustments can be made for mentees who do not attract appropriate mentors on a timely basis. The oversight board review ensures that all relevant factors are considered to balance supply and demand at a particular point in time within a specific geography for mentors and mentees.

In some embodiments, the progress report includes the mentee's current educational status, marital status, various risk factor status, health status, mental status, etc. In some embodiments, the computer processor assigns a point value to each status so as to obtain a total point for each progress report. In some embodiments, the progress report is every 1, 2, 3, 4 or 6 months or other appropriate time interval.

In some embodiments, the financial incentive is provided in the form of (1) a cash payment to the mentor, (2) a contribution to the mentor's retirement plan (e.g., the 401(k) account), (3) a contribution to the mentor's educational savings plan (e.g., the 529 plan and educational savings account), (4) an income tax credit in the form of a federal income tax credit, state income tax credit, city income tax credit, or combinations thereof, and/or "Points" that could be provided by external corporations which want to promote the success of the mentoring program. As used herein, the term "Points" may be generally described as a representation of value that could be converted into goods or services, such as with airline "Points." As used herein, the term "retirement plan" may be generally described as including "Defined Contribution Benefit Plans" with the employee or his/her assignees, etc., as beneficiaries of the plan. These plans include, but are not limited to, 401(k) plans, 403(b) plans, employee stock ownership plans, Simple Individual Retirement Accounts ("Simple IRAs"), simplified employee pension plans (SEPs) and profit sharing plans. The amount of the financial incentive is calculated based on the at-risk subject's behavior and/or the at-risk subject's accomplishments and/or the at-risk subject's income tax payment or estimated lifetime costs to society. In some embodiments, the amount of the financial incentive is calculated based on the at-risk subject's behavior and/or the at-risk subject's personal income tax payment and/or family income tax payment in the past year. The subject's income tax payment may include the federal income tax payment, state income tax payment, city income tax payment or combinations thereof. In some embodiments, the amount of the financial incentive is calculated based on the at-risk subject's projected income tax payment and/or the at-risk subject's estimated lifetime cost to society. In some embodiments, the amount of the financial incentive is calculated based on the at-risk subject's contribution to a retirement plan, such as the 401(k) plan. In some embodiments, the amount of the financial incentive is calculated based on the at-risk subject's contribution to an educational plan, such as the 529 plan. In some embodiments, the amount of the financial incentive is calculated based on one or more factors selected from the at-risk subject's personal income tax payment, the at-risk subject's family income tax payment, the at-risk subject's contribution to a retirement plan (such as the 401(k)) and the at-risk subject's contribution to an educational plan, such as the 529 plan.

In some embodiments, the financial incentive is provided to the mentor as a bonus if the at-risk subject achieves certain goals.

In some embodiments, the method further comprises one or more of the following the steps: obtaining the at-risk subject's projected income tax payment and/or estimated lifetime costs to society, preferably from relevant governmental agencies.

In some embodiments, the method further comprises the steps of obtaining federal and/or local tax (e.g., state and city taxes) payment information from the at-risk subject, and verifying the federal and/or local tax (e.g., state and city taxes) payment information with corresponding governmental agencies. In some embodiments, the method further comprises the step of obtaining permission from the at-risk subject to access the at-risk subject's personal income or family income tax payment information from relevant government agencies.

In some embodiments, the method further comprises the steps of obtaining retirement plan contribution information and/or educational savings plan information from the at-risk subject, and verifying the retirement plan contribution and/or educational plan contribution information with the relevant financial institutions. In some embodiments, the method further comprises the step of obtaining permission from the at-risk subject to access the at-risk subject's retirement plan and/or educational plan information in relevant financial institutions.

In some embodiments, the method further comprises the steps of determining an amount of the cash payment and/or the bonus (in the form of income tax credit) to the mentor, obtaining approval from the oversight board, obtaining approval from relevant governmental agency (e.g., IRS, state or city department of taxation) and processing the amount approved by the governmental agency for payment.

In some embodiments, the method further comprises the step of transmitting a notification of payment to a department, company, agency or financial institution that handles payments to the mentors, wherein the notification causes the department, company, agency or financial institution to process payment to the mentor either reflective of the mentee's progress or as reimbursement for spending by the mentor in support of the mentee.

In some embodiments, the method further comprises the step of transmitting an alert of the cash payment to a mentor to a relevant governmental agency (e.g., IRS) to cause the governmental agency to issue a reimbursement for the cash payment. In some embodiments, the method further comprises the step of transmitting an alert of the issuance of an income tax credit to a mentor to a relevant governmental agency (e.g., IRS) to cause the governmental agency to enter the tax credit into the mentor's tax record.

In some embodiments, the method comprises the steps of obtaining income tax payment information from relevant government agencies or retirement/educational plan contribution information from relevant companies, agencies or institutions, determining an amount of the cash payment and/or the bonus (in the form of income tax credit) to the mentor, obtaining approval from the oversight board, notifying relevant governmental agencies (e.g., IRS, state or city department of taxation) about the approved amount, wherein the notification causes the relevant governmental agency to process payment to the mentor and electronically deliver the payment to a bank account designated by the mentor.

System for Providing Mentoring Service to at-Risk People

Another aspect of the present application relates to a system for providing mentoring service to at-risk people. The system comprises one or more computer processors; and one or more tangible, non-transitory computer readable media accessible by the one or more computer processors, wherein the one or more tangible, non-transitory computer readable media comprise instructions that, when executed by the one or more processors, cause the one or more processors to perform the following functions: receiving, via a user interface of an application executing on the one or more computer processors, a risk profile concerning an at-risk subject, wherein the risk profile comprises a plurality of risk factors; assigning a risk point value to each of the plurality of risk factors based on severity level of the subject's risk factors and a risk point matrix stored on one or more tangible, non-transitory computer readable media accessible by the one or more computer processors; determining a total risk point value of the subject; and when the total risk point value reaches a predetermined threshold value, accepting the at-risk subject as a mentee candidate. In some embodiments, the risk point matrix is determined by evaluating a large scale data base reflecting risks of other subjects compared to their later successes or failures and estimated lifetime costs to society.

In some embodiments, the one or more tangible, non-transitory computer readable media comprise instructions that, when executed by the one or more processors, cause the one or more processors to perform one or more of the following steps: searching, via the one or more computer processors, a mentor candidate database comprising a plurality of mentor profiles, wherein each mentor profile comprises personal data, mentoring experience and a plurality of mentor matching tags; assigning, via the one or more computer processors, at least one mentor candidate to the mentee candidate, wherein the at least one mentor candidate is selected based on a match between the mentee matching tags and the mentor matching tags, wherein the match is performed using a matching algorithm; submitting the at least one assigned mentor candidate to an oversight board for approval; receiving, via the user interface of the application, the at-risk subject's progress report after the establishment of a mentor-mentee relationship; comparing, via the one or more computer processors, the at-risk subject's progress to the progress achieved by other at-risk individuals and their success odds or ex-convict progress and success odds stored on a memory device accessible by the one or more computer processors.

In some embodiments, the one or more tangible, non-transitory computer readable media further comprise instructions that, when executed by the one or more processors, cause the one or more processors to perform one or more of the following steps: assigning a mentor candidate to the at-risk subject, wherein the mentor candidate is selected from a mentor qualification database on a tangible memory device accessible by the one or more computer processor; retrieving, via the one or more computer processors, information about how to reduce risks associated with one or more of the plurality of risk factors from a database stored on the one or more tangible memory device; electronically delivering, via the computer processors, the information to the oversight board and/or a mentor approved by the oversight board; receiving, via a user interface of the application, the at-risk subject's progress report after the establishment of a mentor-mentee relationship; comparing, via the one or more processors, the at-risk subject's progress to at-risk individual success odds or ex-convict success odds stored on a memory device accessible by the one or more computer processors; providing, via the one or more processors, a financial incentive to the mentor based on result of the comparing step; and maintaining, via the one or more processors, a mentor incentive database, wherein the mentor incentive database is stored on a tangible memory device accessible by the one or more processor.

In some embodiments, the one or more tangible, non-transitory computer readable media further comprise instructions that, when executed by the one or more processors, cause the one or more processors to perform one or more of the following the steps: obtaining income tax payment information from relevant government agencies, determining an amount of the cash payment and/or the bonus (in the form of income tax credit) to the mentor, obtaining approval from the oversight board, obtaining approval from relevant governmental agencies (e.g., IRS, state or city department of taxation) and processing the amount approved by the governmental agencies for payment.

In some embodiments, the one or more tangible, non-transitory computer readable media further comprise instructions that, when executed by the one or more processors, cause the one or more processor to perform the step of transmitting a notification of payment to a department, company or agency that handles payments to the mentors, wherein the notification causes the department, company or agency to process payment to the mentor.

In some embodiments, the one or more tangible, non-transitory computer readable media further comprise instructions that, when executed by the one or more processors, cause the one or more processors to perform the step of transmitting an alert of the cash payment to a mentor to a relevant governmental agency (e.g., IRS) to cause the governmental agency to issue a reimbursement for the cash payment. In some embodiments, the method further comprises the step of transmitting an alert of the issuance of an income tax credit to a mentor to a relevant governmental agency (e.g., IRS) to cause the governmental agency to enter the tax credit into the mentor's tax record.

In some embodiments, the one or more tangible, non-transitory computer readable media further comprise instructions that, when executed by the one or more processors, cause the one or more processors to perform the steps of obtaining income tax payment information from relevant government agencies. In some embodiments, the obtaining step described above is replaced with, or combined with, the step of obtaining the at-risk subject's projected income tax payment and/or estimated lifetime costs to society from relevant governmental agencies.

In some embodiments, the one or more tangible, non-transitory computer readable media further comprise instructions that, when executed by the one or more processors, cause the one or more processors to perform the steps of determining an amount of the cash payment and/or the bonus (in the form of income tax credit or cash payment) to the mentor, obtaining approval from the oversight board, notifying relevant governmental agency (e.g., IRS, state or city department of taxation) about the approved amount, wherein the notification causes the relevant governmental agency to process payment to the mentor and electronically deliver the payment to a bank account designated by the mentor.

In some embodiments, the system further comprises one or more of the following databases: at-risk individuals' success odds database, ex-convicts' success odds database, mentors' qualification database, mentors' performance database and mentors' compensation database.

Computer System for Providing Incentive to Mentors of at-Risk Mentees

Another aspect of the present application relates to a computer system for providing incentive to mentors of at-risk mentees. The computer system comprises a computer processor and one or more tangible, non-transitory computer readable media accessible by the computer processor, wherein the one or more tangible, non-transitory computer readable media comprise instructions that, when executed by the one or more processors, cause the one or more processors to perform the steps of: determining a mentee's behavior and progress in a period of time; determining the mentee's income and income tax payments and/or estimated lifetime costs to society during the same period of time; and calculating a financial incentive to the mentee's mentor, wherein the amount of the financial incentive is calculated based on the mentee's behavior and/or income tax payment and/or estimated lifetime costs to society during the period of time using a compensation matrix stored in the one or more tangible computer readable media.

In some embodiments, the tangible computer readable medium comprises instructions stored thereon for selecting mentors and/or mentees based on selection factors including, in the case of mentors, their relative career and lifetime success, their emotional maturity, their job and family status, their ability and willingness to dedicate the time necessary to be a successful mentor, among other factors, and in the case of mentees, their age, family situation, school performance, school attendance, school dropout rates, gang involvement or temptations, drug use, criminal activity, and maturity, among other factors.

In some embodiments, the tangible computer readable medium comprises instructions that, when executed by a processor causes the processor to: (1) receive a selection profile concerning a potential mentor or mentee candidate, wherein the selection profile comprises a plurality of selection factors, qualifications of the mentor and/or risks faced by the mentee; (2) assign a selection point value to the potential candidate based on the qualifications of the mentor, the severity level of the potential mentee candidate's risks and the risk point matrix stored in the memory device, wherein better scores are higher scores; (3) assign additional selection point values to the subject based on other selection factors in the potential candidate's selection profile, wherein better scores are higher scores; (4) determine a total selection point value of the potential candidate; and (5a) if the total candidate point value is equal to or exceeds a predetermined threshold value, accept the potential candidate as a mentor or mentee candidate, or (5b) if the total risk point value is below the predetermined threshold, reject the potential candidate as a mentor or mentee candidate. In some embodiments, the rating system in steps (2) and (3) are designed in such a way that better scores are lower scores, including negative scores, and the potential candidate is accepted as a mentor or mentee candidate if the total candidate point value is equal to or below a predetermined threshold value in step (5a), or is rejected as a mentor or mentee candidate if the total candidate point value exceeds a predetermined threshold value in step (5b).

In some embodiments, the tangible computer readable medium stores estimated and actual costs to society associated with children who "fail" to become productive. Examples of such costs include, but are not limited to, the costs of welfare, food stamps, unemployment payments, Medicaid, teenage pregnancy, drug use, crime, prison, lack of income tax payments, failing to graduate from high school, and a risk point matrix. In some embodiments, the tangible computer readable medium comprises instructions when executed by a processor causing the processor to: (1) receive a risk profile concerning the mentee subject, wherein the risk profile comprises a plurality of risk factors including the severity level of the subject's probability of dropping out of school or failing in a variety of other ways that will be expensive to society in terms of actual dollars and/or opportunity costs compared to what the mentee might achieve with appropriate guidance; (2) evaluate the expected value of the mentee's life, from society's point of view and compare it to what might be achieved with appropriate guidance; (3) recommend a compensation factor to be assigned to the mentee's mentor that will provide a strong incentive to the mentor while allowing society to retain a significant benefit as well; and (4) recommend a share of the income taxes that will be paid by the mentee and that will then be paid to the mentor by the tax authorities in recognition of mentor's role in ensuring the mentee's success or recommend a share of the improved expected value of the mentee's life that will then be paid to the mentor by government agencies in recognition of the mentor's role in ensuring the mentee's improved success and lower than expected costs to society.

In some embodiments, the one or more tangible, non-transitory computer readable media store income and income tax data regarding the mentee and/or the mentee's family in order to: (1) provide a basis for payments to mentors as compensation for their services; (2) provide a periodic basis for analysis of mentee's productivity and success relative to the Success Odds analysis originally projected based on the mentee's risk assessment prior to becoming a mentee; and (3) provide a basis for analysis of mentor's productivity and success relative to the Success Odds analysis originally projected based on the mentee's risk assessment prior to becoming a mentee.

In some embodiments, the tangible, non-transitory computer readable media further comprises instructions when executed by a processor causing the processor to obtain federal and/or local tax (e.g., state and city taxes) payment information from the at-risk subject, and verify the federal and/or local tax (e.g., state and city taxes) payment information with corresponding governmental agencies. In some embodiments, the tangible, non-transitory computer readable media further comprises instructions when executed by a processor causing the processor to obtain permission from the at-risk subject to access the at-risk subject's personal income or family income tax payment information in relevant government agencies.

In some embodiments, the tangible, non-transitory computer readable media further comprises instructions when executed by a processor causing the processor to obtain retirement plan contribution information and/or educational savings plan information from the at-risk subject, and verify the retirement plan contribution and/or educational plan contribution information with the relevant financial institutions. In some embodiments, the tangible, non-transitory computer readable media further comprises instructions when executed by a processor causing the processor to obtain permission from the at-risk subject to access the at-risk subject's retirement plan and/or educational plan information in relevant financial institutions.

In some embodiments, the tangible, non-transitory computer readable media stores recidivism rates for ex-convicts and compares them to recidivism rates for ex-convicts who become mentees and keeps track of mentor actions designed to help their mentees become successful and keeps track of mentee income and income tax payments in order to: (1) provide a basis for payments to mentors whose mentees avoid future crimes and future prison sentences; (2) provide a basis for determining which mentor actions and strategies are most successful for which types of mentees; (3) provide a basis for determining which mentor qualities and/or qualifications are most helpful for which types of mentees; (4) assign payments to mentors reflecting the time period the mentees have avoided criminal behavior and/or the income tax payments made by the mentees and/or their costs to society; (5) provide an ongoing database which can be analyzed in order to assign future mentor compensation rates based on the success of the mentoring program; and (6) provide a basis for analyzing the overall costs of recidivism, in terms of court costs, prison costs, and society's costs due to the crimes being committed. The higher amounts of income tax paid by ex-convicts who become mentees may be only a small fraction of the overall benefit to society that is achieved with this program.

Tangible, Non-Transitory Computer Readable Medium

Another aspect of the present application relates to a tangible, non-transitory computer readable medium. The tangible, non-transitory computer readable medium comprises instructions stored thereon for providing mentoring service to at-risk people, the instructions when executed by a processor causing the processor to perform the steps of: receiving, via a user interface of an application executing on the computer processor, a risk profile concerning an at-risk subject, wherein the risk profile comprises a plurality of risk factors; assigning a risk point value to each of the plurality of risk factors based on severity level of the subject's risk factors and a risk point matrix stored on one or more tangible, non-transitory computer readable media accessible by the processor; determining a total risk point value of the subject; and when the total risk point value reaches a predetermined threshold value, accepting the at-risk subject as a mentee candidate.

In some embodiments, the risk point matrix has been determined by evaluating a large scale data base reflecting risks of other subjects compared to their later successes or failures and costs to society.

In some embodiments, the tangible, non-transitory computer readable medium comprises instructions that, when executed by a computer processor, cause the computer processor to perform one or more of the following steps: searching, via computer processor, a mentor candidate database comprising a plurality of mentor profiles, wherein each mentor profile comprises personal data, mentoring experience and a plurality of mentor matching tags; assigning, via the computer processor, at least one mentor candidate to the mentee candidate, wherein the at least one mentor candidate is selected based on a match between the mentee matching tags and the mentor matching tags, where in the match is performed using a matching algorithm; submitting the at least one assigned mentor candidate to an oversight board for approval; receiving, via the user interface of the application, the at-risk subject's progress report after the establishment of a mentor-mentee relationship; comparing, via the computer processor, the at-risk subject's progress to the progress achieved by other at-risk individuals and their success odds or ex-convict progress and success odds stored on a memory device accessible by the computer processor.

In some embodiments, the tangible, non-transitory computer readable medium further comprises instructions when executed by a processor causing the processor to perform the steps of: assigning a mentor candidate to the at-risk subject, wherein the mentor candidate is selected from a mentor qualification database on a tangible, non-transitory memory device accessible by the processor; retrieving, via the one or more computer processors, information about how to reduce risks associated with one or more of the plurality of risk factors from a database stored on the one or more tangible memory device; and electronically delivering, via the computer processors, the information to the oversight board and/or a mentor approved by the oversight board.

In some embodiments, the tangible non-transitory computer readable medium further comprises instructions when executed by a processor causing the processor to perform the steps of: receiving, via a user interface of the application, the at-risk subject's progress reports after the establishment of a mentor-mentee relationship; comparing, via the one or more processors, the at-risk subject's progress to at-risk individual success odds or ex-convict success odds stored on a memory device accessible by the one or more computer processors; providing, via the one or more processors, a financial incentive to the mentor based on result of the comparing step; and maintaining, via the one or more processors, a mentor incentive database, wherein the mentor incentive database is stored on a tangible, non-transitory memory device accessible by the one or more processor.

In some embodiments, the tangible, non-transitory computer readable media further comprises instructions when executed by a processor causing the processor to obtain federal and/or local tax (e.g., state and city taxes) payment information from the at-risk subject, and verify the federal and/or local tax (e.g., state and city taxes) payment information with corresponding governmental agencies. In some embodiments, the tangible, non-transitory computer readable media further comprises instructions when executed by a processor causing the processor to obtain permission from the at-risk subject to access the at-risk subject's personal income or family income tax payment information in relevant government agencies.

In some embodiments, the tangible, non-transitory computer readable media further comprises instructions when executed by a processor causing the processor to obtain retirement plan contribution information and/or educational savings plan information from the at-risk subject, and verify the retirement plan contribution and/or educational plan contribution information with the relevant financial institutions. In some embodiments, the tangible, non-transitory computer readable media further comprises instructions when executed by a processor causing the processor to obtain permission from the at-risk subject to access the at-risk subject's retirement plan and/or educational plan information in relevant financial institutions.

FIG. 1 is a block diagram illustrating exemplary hardware components that may be used for implementing aspects of the systems and methods for using incentives to motivate mentoring activities for at-risk people. A computer system 100 may include and execute programs to perform functions described herein, including steps of method described above. While only one processor 114 is shown in FIG. 1, it is understood that the computer system 100 may include multiple processors. Additionally, the system 100 may include multiple networked computers. Further, a mobile device that includes some of the same components of computer system 100 may perform steps of the method described above. Computer system 100 may connect with a network 118, e.g., Internet, or other network, to receive inquires, obtain data, and transmit information (e.g., to a user work station or other user computing device) as described above.

Computer system 100 typically includes a memory 102, a secondary storage device 112, and a processor 114. Computer system 100 may also include a plurality of processors 114 and be configured as a plurality of, e.g., bladed servers, or other known server configurations. Computer system 100 may also include an input device 116, a display device 110, and an output device 108.

Memory 102 may include RAM or similar types of memory, and it may store one or more applications for execution by processor 114. Secondary storage device 112 may include a hard disk drive, floppy disk drive, CD-ROM drive, or other types of non-volatile data storage. Processor 114 may include multiple processors or include one or more multi-core processors. Any type of processor 114 capable of performing the calculations described herein may be used. Processor 114 may execute the application(s) that are stored in memory 102 or secondary storage 112, or received from the Internet or other network 118. The processing by processor 114 may be implemented in software, such as software modules, for execution by computers or other machines. These applications preferably include instructions executable to perform the functions and methods described above and illustrated in the Figures herein. The applications may provide graphic user interfaces (GUIs) through which users may view and interact with the application(s).

Also, as noted, processor 114 may execute one or more software applications in order to provide the functions described in this specification, specifically to execute and perform the steps and functions in the methods described above. Such methods and the processing may be implemented in software, such as software modules, for execution by computers or other machines.

Input device 116 may include any device for entering information into computer system 100, such as a touch-screen, keyboard, mouse, cursor-control device, microphone, digital camera, video recorder or camcorder. Input device 116 may be used to enter information into GUIs during performance of the methods described above. Display device 110 may include any type of device for presenting visual information such as, for example, a computer monitor or flat-screen display (or mobile device screen). Output device 108 may include any type of device for presenting a hard copy of information, such as a printer, and other types of output devices include speakers or any device for providing information in audio form.

Examples of computer system 100 include dedicated server computers, such as bladed servers, personal computers, laptop computers, notebook computers, palm top computers, network computers, mobile devices, or any processor-controlled device capable of executing a web browser or other type of application for interacting with the system. If computer system 100 is a server, server 100 may not include input device 116, display device 110 and output device 108. Rather, server 100 may be connected, e.g., through a network connection to a stand-alone work station (another computer system) that has such devices.

Although only one computer system 100 is shown in detail, the computer system 100 may use multiple computer systems or servers as necessary or desired to support the users, as described above. Aspects may also use back-up or redundant servers to prevent network downtime in the event of a failure of a particular server. In addition, although computer system 100 is depicted with various components, one skilled in the art will appreciate that the server can contain additional or different components. In addition, although aspects of an implementation consistent with the above are described as being stored in memory, one skilled in the art will appreciate that these aspects can also be stored on or read from other types of computer program products or computer-readable media, such as secondary storage devices, including hard disks, floppy disks, or CD-ROM, or other forms of RAM or ROM. Computer-readable media may include instructions for controlling a computer system, such as the computer system 100, to perform a particular method, such as methods described above.

Figure 2:
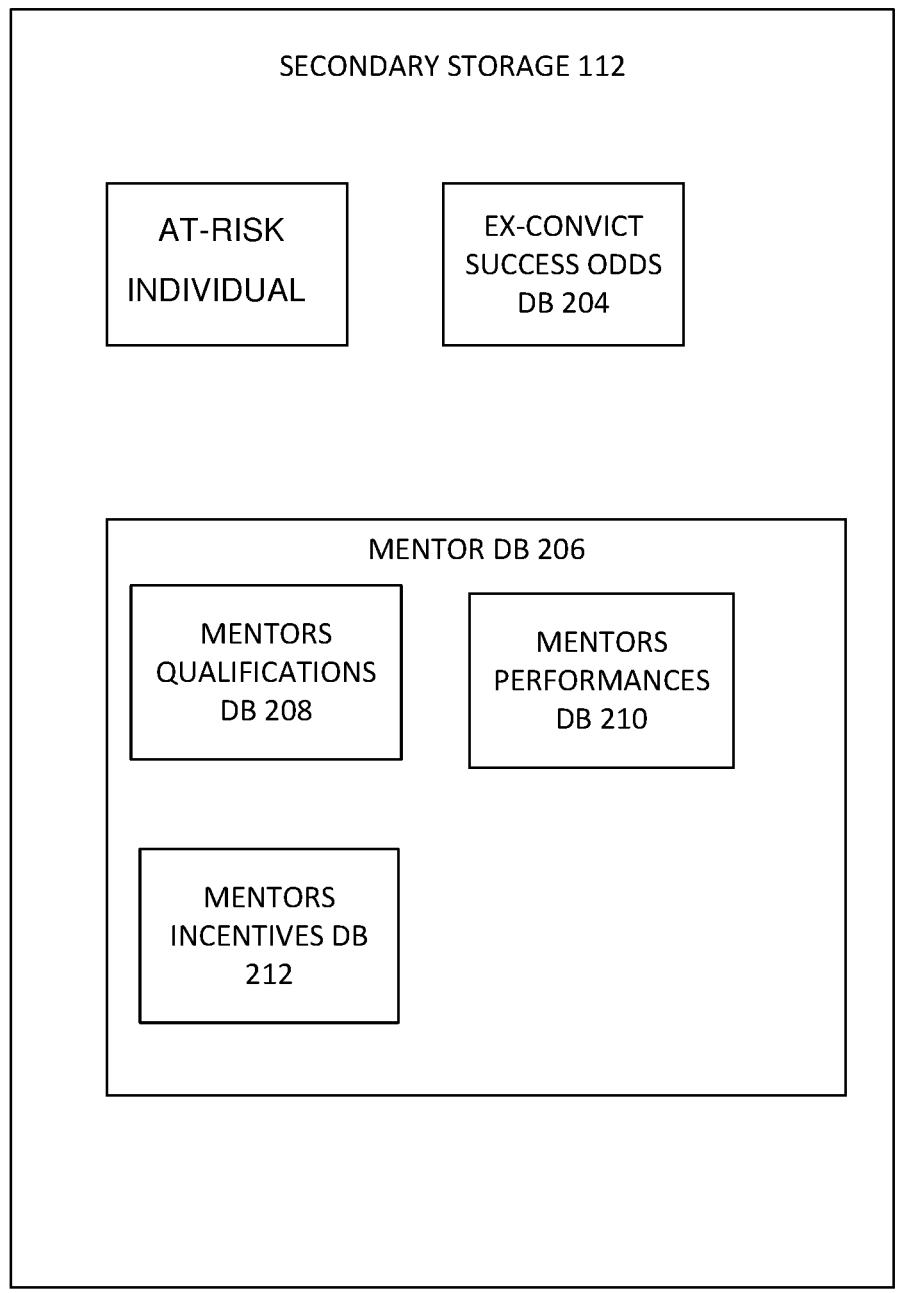
FIG. 2 shows an embodiment of the database structure of the present application.

FIG. 2 shows a plurality of databases (DB) that may be stored in either memory 102, secondary storage 112, or a combination of memory 102 and secondary storage 112. For purposes of description only, this description will assume that the plurality of databases are stored on the secondary storage 112. The plurality of database may include any suitable database, such as a document-oriented database, a full-text database, a spatial database, a distributed database, and a relational database. One of ordinary skill in the art would readily recognize that other types of databases may be used.

At-Risk Individual's Success Odds Database

In one aspect of this disclosure, a first database is an at-risk individual's success odds DB 202. The at-risk individual success odds DB 202 may store a plurality of at-risk individuals' records. The at-risk individual success odds DB 202 may be used to store various attributes or characteristics about each individual and his or her life situation stored in DB 202. The various stored attributes or characteristics may comprise a risk profile for each individual stored in the children success odds DB 202. For example, the at-risk individual success odds DB 202 may include attributes or characteristics such as the individual's IQ (intelligence quotient), the individual's prior success in school (attendance rates, grades, teacher assessments, discipline problems, etc.), the individual's family income, the neighborhood or ZIP code of where the individual lives, the school the individual attends, the dropout rate of the school the individual attends, the family status of the individual's family, the success of the individual's siblings, the individual's neighborhood's crime rates, the individual's neighborhood's gang activity, and the individual's neighborhood's drug use. In some embodiments, the Success Odds (SO) is calculated based on the following formula:

$$SO=f(a,b,c,d,e,f,g,h,i,j)=Aa+Bb+Cc+Dd+Ee+Ff+Gg+Hh+Ii+Jj+Kk+Ll$$

wherein a=IQ, b=family income, c=neighborhood assessment, d=school assessment, e=family status, f=sibling success, g=crime rate, h=local drug use, i=dropout rate, j=school success, k=neighborhood gang activity, l=other factors, and wherein the weight of each contributing factor may be modified by a modifying factor (e.g., A, B, C, D, E, F, G, H, I, J, K, or L).

One of ordinary skill in the art would readily recognize that other attributes or characteristics may be stored in the at-risk individual success odds DB 202. Based on these attributes or characteristics, the system 100 may generate a risk point value for each individual using a probability of various life events. For purposes of description only, the remainder of this disclosure will assume that the higher the risk point value, the more likely the individual is at-risk. One of ordinary skill in the art would readily recognize that the risk point value may be defined in such a manner that, the lower the risk point value, the more likely the individual is, at-risk. For example, the various life events may include graduating from high school, graduating from college, becoming a contributing member of society, future drug use, future criminal conviction, future unemployment, future welfare assistance, or future premature death. One of ordinary skill in the art would readily recognize that other life events may be calculated using the attributes or characteristics about each individual stored in the at-risk individual's success odds DB 202. To generate the risk point value for each individual, the system 100 may assign a certain number of points for each of the life events described above. The system 100 may then simply add all of the points to generate the risk point value. Alternatively, the system 100 may assign a weighting factor to each of the life events. The system 100 may then generate the risk point value using weighting factors and the points for each life event described above. Likewise, there may be attributes which correlate in a way that affects the risks for some at-risk individuals. In this case, for example, an individual whose siblings all did well may not be affected by gang activity or drug use in the neighborhood; however, if siblings were susceptible to such dangers, then the weight of these risks would be magnified. So the simplistic formula above may become more complicated as analysis of the available data demonstrates interrelationships of risk factors that need to be evaluated by the computer system.

In another aspect of this disclosure, the system 100 may add to the risk point value that was calculated based on the life events described above. For example, the system 100 may factor in the gender, the individual's non-academic interests, the section of the country in which the individual lives, and the individual's overall appearance. One of ordinary skill in the art would readily recognize that other non-life events may be factored in by the system 100. A certain number of risk points may be assigned to these non-life events. These risk points may then be added to the risk points based on life events. Alternatively, these risk points may also be weighted and then added to the risk points based on life events. In some embodiments, the at-risk individual's success odds DB contains a sub-database for at-risk children.

Ex-Convict's Success Odds Database

In one aspect of this disclosure, a second database may be an ex-convict success odds DB 204. The ex-convict success odds DB 204 may function similarly to the at-risk individual's success odds DB 202 as described above with the exception that the DB is for ex-convicts rather than at-risk individuals in general. The ex-convict success odds DB 204 may be used to store various attributes or characteristics about each ex-convict stored in the DB 204. The various stored attributes or characteristics may comprise a risk profile for each ex-convict stored in the ex-convict success odds DB 204. For example, the ex-convict success odds DB 204 may include attributes or characteristics such as the ex-convict's committed crime, the number of years in prison, the ex-convict's education level, the ex-convict's workplace skills, the ex-convict's family support system, the ex-convict's personality, which may be assessed by a trained professional, the ex-convict's drug use history, the ex-convict's gang involvement history, the ex-convict's behavior while in prison, and other factors that may be used by evaluating historical recidivism data. Based on these attributes or characteristics, the system 100 may generate a risk point value for each ex-convict. For purposes of description only, the remainder of this disclosure will assume that the higher the risk point value, the more likely the ex-convict is at-risk. One of ordinary skill in the art would also readily recognize that the risk point value may be defined in such a manner that, the lower the risk point value, the more likely the ex-convict is, at-risk. One of ordinary skill in the art would also readily recognize that other attributes or characteristics may be stored in the ex-convict success odds DB 204. To generate the risk point value for each ex-convict, the system 100 may assign a certain number of points for each of the attributes or characteristics described above. The system 100 may then simply add all of the points to generate the risk point value. Alternatively, the system 100 may assign a weighting factor each of the attributes or characteristics. The system 100 may then generate the risk point value using weighting factors and the points for each attribute or characteristic described above. In some embodiments, this analysis is completed while the individual is still in prison.

In some embodiments, the Success Odds of ex-convicts ($SO_{ExCon}$) are evaluated based on the following formula:

$$(SO_{ExCon}) = f(a,b,c,d,e,f,g,h,i) = Aa + Bb + Cc + Dd + Ee + Ff + Gg + Hh + Ii$$

Wherein a=crime committed, b=years in prison, c=education, d=workplace skills, e=family support system, f=personality assessment by a trained professional, g=drug use history, h=gang involvement history, i=other factors found by evaluating historical recidivism data, and wherein the weight of each contributing factor may be modified by a modifying factor (e.g., A, B, C, D, E, F, G, H or I). As with the formula for the at-risk individuals, the equation above may need to be significantly more complicated if it is determined that various factors are interrelated in their effects.

If the Success Odds are below a certain level, then clearly intervention by a mentor could be very valuable. As the mentor-mentee relationship continues, data could also be collected regarding the impact of mentors on various "types" of at-risk individual, for example the impact of mentoring on the at-risk individuals with Success Odds of 20-30% vs. the impact of mentoring on the at-risk individuals with Success Odds of 0-10%. In some embodiments, the amount of mentor incentive varies depending on the magnitude of the challenge that the mentor will face in helping his or her mentee to succeed. In some embodiments, mentors are assigned to mentees of the same gender. In some embodiments, mentors are assigned to mentees of different gender. In some embodiments, mentors are assigned to mentees of the same ethnicity. In other embodiments, mentors are assigned to mentees of different ethnicity. Other factors to be considered for mentor/mentee pairing include regularity of interaction, geographic distance, the family situation of the mentor, the job status of the mentor, etc. In some embodiments, the system analyzes periodically the past mentor/mentee pairing data and results and determines what seems to be working and what seems to be failing. The knowledge accumulated in the analysis is used to improve future pairings as well as to advise current mentors and mentees about which behavior characteristics they should consider employing for best results.

The risk of recidivism for ex-convicts can be calculated in a way similar to the Success Odds of the at-risk individuals. In some embodiments, the mentor-mentee relationship is established with an in-prison mentor while an ex-con mentee is in prison and the mentoring continues with an outside mentor after the mentee is released from the prison. In some embodiments, the in-prison mentor is selected from people who work in prison and the outside mentor is selected from people who work outside of prison. In some embodiments, the in-prison mentors are paid based on the recidivism rates of the ex-con mentees and the outside mentors are paid based on the ex-con mentees' income tax payments. In some embodiments, the in-prison mentor and the outside mentor is the same person.

Mentors' Databases

In one aspect of this disclosure, a third database may be the mentors' DB 206. The mentors' DB 206 may be comprised of a plurality of databases. The mentors' DB may be comprised of, for example, a mentor's qualifications DB 208, a mentor's performances DB 210, and a mentor's incentives DB 212. One of ordinary skill in the art would readily recognize that more or fewer databases may be used.

The mentors' qualifications DB 208 may be used to store a plurality of mentor records. For example, the mentors' qualifications DB 208 may store various attributes or characteristics about each mentor stored in mentors' qualifications DB 208. For example, the mentors' qualifications DB 206 may include attributes or characteristics such as each mentor's education, profession, job history, criminal history, health history, drug use history, leadership roles or positions, family status, or any other attributes or characteristics that may be helpful in being a successful mentor. The mentors' qualifications may also include training classes attended, relevant books read, or tests passed all of which may be relevant in preparing a mentor for success. A mentor profile may be generated for each mentor using these attributes or characteristics. One of ordinary skill in the art would readily recognize that other attributes or characteristics may be used when generating the mentor profiles. There may also be "free-form" entries, such as leadership positions held within the mentor's community or letters of recommendations or references provided by the mentor attesting to, for example, the mentor's character. The mentors' qualifications may be periodically updated to account for, for example, new references or leadership positions. Longer term, each mentor's track record of success or failure with his or her mentees will also be an important factor in judging the mentor's qualifications in the future. Keeping track of each of these elements on a massive scale should allow the ability over time to correlate which seem to have an effect on overall mentoring success.

The mentors' qualifications DB 208 may also store potentially disqualifying attributes or characteristics. For example, if a potential mentor volunteers for the system 100, then the potential mentor may be added to the mentor DB 206. However, if it is later found out that the potential mentor is, for example, an alcoholic, a drug user, a criminal or a child molester, the potential mentor would then be disqualified.

In addition to qualifications, the mentors' qualifications DB 208 may also include suitability measures for a given mentor-mentee pair. For example, before a mentor is assigned to a mentee, the mentee and mentor may audition each other for, for example, compatibility. The mentors' qualifications DB 208 and the at-risk individual's success odds DB 202 may also store the results of such an audition. Moreover, the mentee may reject a mentor after a mentor-mentee relationship has been established. In such a case, the mentors' qualifications DB 208 may include a note indicating that the mentor is not suitable for the mentee. Depending on the contents of that note, the mentor may not be considered suitable for any future mentee. Depending on the timing of that note and the reasons behind it, the mentor's right to any future payments may be eliminated or adjusted.

The mentors' performances DB 210 may also be used to store a plurality of mentor records. For example, the mentors' performances DB 210 may store records related to how well the mentors are performing. One way to assess how well the mentors are performing is by comparing results of the mentees to the at-risk individuals' success odds or the ex-convicts' success odds. The greater the at-risk individuals' or ex-convicts are succeeding compared to the respective success odds, the better the mentors are performing. Another way the system 100 may assess how well the mentors are performing is by including reports from various parties. For example, the mentee's parents, teachers, or other interested parties may provide reports discussing how well the mentor is having an impact on the mentee. One of ordinary skill in the art would readily recognize that other performance metrics may be used to determine the efficacy of the mentor. The performance metrics may be collected periodically. In some embodiments, various alerts are provided by the system if results are significantly positive or negative so that appropriate action can be taken to either duplicate or eliminate the behavior reported.

Additionally, the mentors' performances DB 210 may include a plurality of problem-solution pairs. For example, if a mentor reports that a certain solution worked well for a mentee in a given situation, this may be noted in the mentors' performances DB 210. Alternatively, if a mentor reports that a certain solution did not work well for a mentee in a given situation, this also may be noted in the mentors' performances DB 210. Such problem-solution pairs may be useful for other mentor-mentee relationships.

The system 100 may also include an oversight board to review and approve a mentor-mentee pair, and to track how well the mentors are performing. The board may use the information in the mentors' performances DB 210 to perform the tracking. In addition to tracking how well the mentors are performing, the board may assign a mentor to a mentee. The assignment may take place based on, for example, mentee success odds, mentor qualifications, and mentor performances. Additionally, the board may limit the number of mentees a mentor may have. For example, if a mentor is new and has not yet proven that he is a good mentor, the board may limit the number of mentees the mentor may have at any given time initially. If the mentor performs well, then the board may increase the number of mentees the mentor may have. In any case, it is likely that the allowable number of mentees should grow for each mentor as the mentor demonstrates success and as mentees perhaps require fewer hours per week as they mature and succeed with their lives. In some embodiments, the oversight board is also responsible for reviewing and approving mentor's compensation.

In some embodiments, the system 100 may retrieve information about the qualifications of potential mentors in general and/or their specific qualifications with respect to mentoring a specific mentee candidate or type of mentee candidate, and electronically or otherwise deliver the information to the oversight board which will be responsible for approving the assignment of a mentor to the particular mentee. The system 100 may also electronically or otherwise deliver some aspects of the mentor information to potential mentees or their parents or guardians and obtain a response from the potential mentees about their willingness to work with a particular mentor.

In some embodiments, the system 100 evaluates or provides information to the oversight board to evaluate the probability that the potential mentor will be successful in reducing the various risk factors associated with one or more potential mentees. Factors to be analyzed will include their education, family status, age, non-work interests, jobs held, criminal history, health, drug use, leadership, ethnicity, religion, or other personality trait track records. Their position in the community and references from respectable people testifying to the qualifications of the mentors could also be important. By tracking mentors' qualifications and personal and professional attributes compared to their performance over time, the data will become available to provide future guidance about which potential mentors would be most effective. Correlating these results with the attributes of their respective mentees could also be productive. The best mentor for person X might be far different than the best mentor for person Y.

In some embodiments, the system 100 electronically tracks mentors' performance in guiding their mentees. These could include statistics about the success of the mentees relative to their initial Success Odds and could include reports from the mentees and/or their parents or teachers or other interested parties. Whether data should be collected weekly or monthly or in some other periodic fashion will also be influenced by an ongoing analysis of the data. Higher frequency early in the relationship will certainly make sense, but the time interval may be extended based on stable positive relationships and progress. In some embodiments, data is collected weekly in the first 1, 2, 3, 4, 5 or 6 months in the mentor-mentee relationship. The time interval for data collection is extended to 2 weeks, 1, 2, 3 or 6 months based on the progress of the mentor-mentee relationship. Of course, learning both the good and the bad aspects of each relationship can be equally important. In some cases, even the mentors may need mentors if particularly challenging situations arise. Mentors are encouraged to reach out for assistance if they are facing challenging issues. The system 100 will provide the option for the mentor to read proposed advice or access to a live person for a brief conversation or attend a class to learn about the issue or request an expert to participate in a future mentee meeting. In some embodiments, each mentee has his/her own database. Having a large scale database that addresses a wide range of possible problems and solutions will be critical in order to get the best results for each mentee on a timely basis. Having a specific database for each mentee will also be important in order to ensure appropriate progress is being made and in order to alert authorities if mentor or mentee behavior appears to be inappropriate or unsuccessful in any way or evidence suggests that the current mentor/mentee relationship needs to be terminated or modified in some way. In some embodiments, the system 100 electronically tracks the overall results of the mentoring process.

The mentors' incentives DB 212 may be used to store a plurality of mentor records. The mentor records stored in the mentors' qualifications DB 208, the mentors' performances DB 210, and the mentors' incentives DB 212 may all be identical. The system 100 may incentivize mentors for their efforts. For example, the mentor may receive a portion of his mentee's tax payments. In this way, the mentor and even the mentor's family and friends may be incentivized to maximize the financial well-being of his mentee. There may be some adjustments to this incentive, however. For example, women generally have lower incomes than men. Accordingly, there may be an adjustment factor to correct for such income inequalities. Alternatively, or additionally, the mentor may be compensated based on the mentee's household tax payments. For example, the mentee could be woman who becomes a successful but non-working mother. The mentor may have had a large part to play in that success.

However, since the woman is non-working, she does not generate any taxable income. Therefore, sharing in the tax payments based on household income may be a way to appropriately compensate the mentor.

The amount of the financial incentive to be provided to the mentor may reflect the initial estimates of the risk level faced by the mentee as determined by comparing the mentee's risk factors to those of the historical data base accumulated in the computer system and assessing the likely future performance of the mentee based on those relative risk comparisons. The potential costs of crime, prison, welfare, and estimated cost to society for some people with those risk factors are balanced against the positive impact of those who succeed despite the risk factors. Depending on how severe the risk factors may be, the share of the future income tax payments could be very high while still providing a long term benefit for society if the mentor is successful. In some embodiments, the amount of the mentor's incentive is calculated as a percentage of the mentee's personal income tax payment, the mentee's family income tax payment, the mentee's projected income tax payment, the mentee's projected family income tax payment, the mentee's retirement plan contributions and/or the mentee's education plan contributions. The tax payment may include the federal tax payment, state tax payment and/or city tax payment.

The system 100 may also provide for additional bonuses. These additional bonuses may be based, for example, on specific goals, such as graduating from high school, achieving a specific grade point average, gaining acceptance at a college, avoiding teen pregnancy, drug use, gang activity, or crime. Such goals may not result in any taxable income. Therefore, one way to compensate the mentor may be a tax deduction. The tax deduction may depend on how well the mentee is doing in regard to the specific goal. This could be, for example, a deduction on mentor's tax bills upon their mentee reaching a certain age without having succumbed to any of these temptations or for having achieved some of these goals. In some embodiments, a database is constructed that tracked the performance of the mentees on these and other key factors. In some embodiments, the bonus is provided as an income tax credit to the mentor, wherein the amount of the income tax credit is calculated based on the at-risk subject's behavior and/or the at-risk subject's income tax payment, the at-risk subject's retirement plan contributions and/or the at-risk subject's education plan contributions. In some embodiments, the tax credit is a federal income tax credit, state income tax credit, city income tax credit, or combinations thereof. In some embodiments, the bonus is a direct payment to the mentor, which may or may not be considered taxable income. In some embodiments, the bonus is a direct payment or a payment of Points based on the mentee's estimated costs to society compared to the mentee's forecasted costs to society for the mentee over some period of time. These points may be provided by one or more corporations or other entities which desire to support the mentoring activities and promote use of their products and/or services. In some embodiments, the bonus is a direct payment or payment of Points based on the difference between the mentee's estimated costs to society at the beginning of a period of time and the mentee's estimated costs to society at the end of a period of time. In some embodiments, the system 100 calculates the projected income tax payment of the mentee based on verified income information provided by the mentee.

In some embodiments, the system 100 electronically obtains income tax payment information, retirement plan contribution information and/or education plan contribution information from relevant government agencies and/or financial institutions, determines an amount of the cash payment and/or the bonus (in the form of income tax credit) to the mentor based on the income tax payment information, retirement plan contribution information and/or education plan contribution information, and obtains approval from the oversight board and/or the relevant governmental agencies (e.g., IRS, state or city department of taxation).

In some embodiments, the system 100 processes the amount approved by the governmental agency for payment to the mentor. In some embodiments, the system 100 transmits a notification of payment to a department, company or agency that handles payments to the mentors, wherein the notification causes the department, company or agency to process payment to the mentor. In some embodiments, the system 100 further transmits an alert of the cash payment to a mentor to a relevant governmental agency (e.g., IRS) to cause the governmental agency to issue a reimbursement for the cash payment.

In some embodiments, the system 100 transmits an alert of the issuance of an income tax credit to a mentor to a relevant governmental agency (e.g., IRS) to cause the governmental agency to enter the tax credit into the mentor's tax record.

In some embodiments, the system 100 obtains income tax payment information, retirement plan contribution information and/or education plan contribution information from relevant government agencies or financial institutions, determines an amount of the cash payment to the mentor, obtains approval from the oversight board, notifies relevant governmental agencies (e.g., IRS, state or city department of taxation) about the approved amount, wherein the notification causes the relevant governmental agency to process payment to the mentor and electronically deliver the payment to a bank account designated by the mentor.

Additionally, a convict who is about to be released from prison or an ex-convict who has already been released from prison may have multiple mentors, such as two. For example, one mentor may have worked with the mentee when he or she was inside the prison and another mentor may be outside the prison. The two mentors may be compensated differently. For example, the mentor inside the prison may be compensated based on the mentee's recidivism. The mentor outside the prison may be compensated based on the mentee's income tax payments and/or avoidance of costs to society (which could also include recidivism).

The initial database describing the Success Odds and the mentor share of future payments will be very important in focusing the work while properly motivating the mentors. In some embodiments, the system 100 tracks the both the mentees and the mentors in order to determine the success of the relationship and identifies the key elements of the success or lack thereof. Any particular mentor may look good on paper, but only time and the database will be able to determine the true efficacy of his or her activities. Both future mentors and mentees may have an opportunity to learn from the success and failures of their predecessors if they are captured properly in the computer system and analyzed carefully.

Mentee Safety and Program Oversight

It will be crucial to ensure that vigilant oversight of this process is in place. When launched on a massive scale, care must be taken to deal with the fact that child molesters, criminals or simply ineffective mentors may find their way into the system. Accordingly, in some embodiments, a database and/or emergency information system is constructed so that any improper behavior can be instantly reported and dealt with effectively. The contracts signed with mentors may include clauses that eliminate their right to future payments if improper behavior occurs. Likewise, mentees are provided with the right to audition mentors and/or reject them down the road if they are not comfortable that the relationship is appropriate or productive for them. Keeping a careful database of mentor candidates that includes reports of their success and failures will be critical to ensure that mentees are both protected and given the best odds of future success. In some embodiments, the database would be a nationwide database to ensure that "bad apples" identified in one jurisdiction do not later take root in another. Likewise, it will no doubt be true that some mentors will develop spectacular ideas that should be quickly copied across the land. Collecting and sharing the bad and the good stories from this database will both be extremely valuable.

In some embodiments, another associated database can track the overall mentor review process. An oversight entity may oversee the mentors' behavior and approve each assignment and review the success of the assignment on an ongoing basis. One can imagine various types of misbehavior that could take place in this sort of bureaucracy, so it will be important to track various metrics to ensure the best possible results while encouraging whistle blowers or contrary points of view that may, upon inspection, have great merit. Having an extensive database that is carefully mined on a regular basis will help to ensure that the process gets the best results. Keeping track of drug use, crime, employment rates, graduation rates, dropout rates, teen pregnancy, and other measures of success and failure will be important in assessing the ongoing qualifications of the various mentors. In some embodiments, a new mentor is limited to just 1 or 2 or a few mentees until he or she can establish his or her credentials through the success of the mentees.

Figure 3:
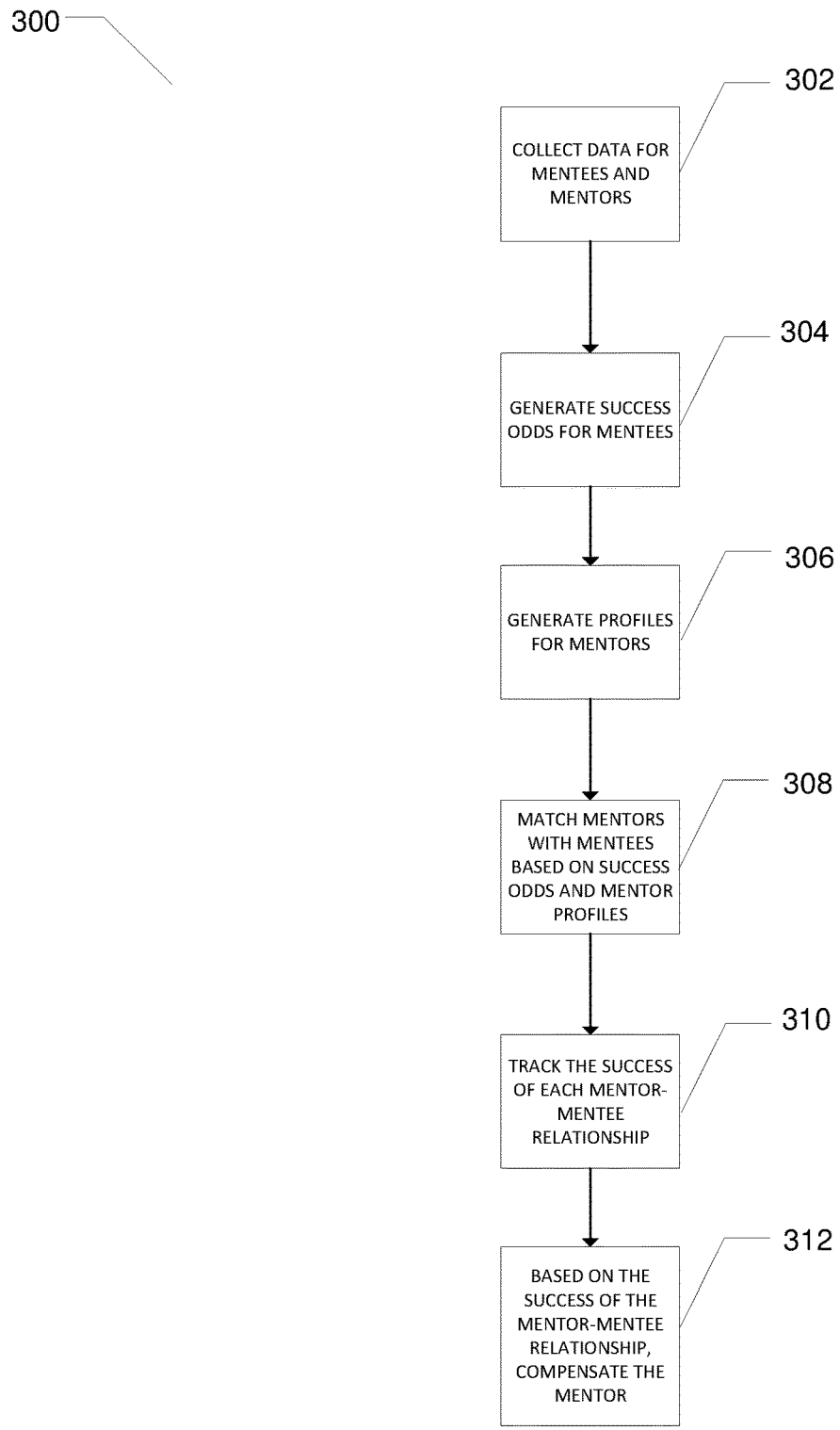
FIG. 3 is a flow chart showing exemplary steps of the method of the present application.

FIG. 3 is a flowchart showing a method 300 to carry out the system 100, according to one aspect of this disclosure. The method 300 may start at block 302. At block 302, the system 100 may collect data for mentees and mentors. The collected data may be used to populate the at-risk individual's success odds DB 202, the ex-convict success odds DB 204, and the mentor DB 206, for example. After block 302 is complete, the method 300 may proceed to block 304.

At block 304, the system 100 may generate success odds for the mentees. The mentees may be, for example, an at-risk individual or ex-convicts. The success odds for the mentees may be calculated as described above in reference to FIG. 2. After block 304 is complete, the method 300 may proceed to block 306.

At block 306, the system 100 may generate profiles for the mentors. The system may generate profiles for the mentors using the information described above in reference to FIG. 2. After block 306 is complete, the method 300 may proceed to block 308.

At block 308, the system 100 may match the mentors with the mentees. The matching may be carried out entirely by the system 100, entirely by the oversight board described above, or by a combination of the system and the oversight board. After block 308 is complete, the method 300 may proceed to block 310.

In some embodiments, the system 100 comprises a matching module that includes software and/or logic for matching a mentor with a mentee based on the mentee's profile and the mentor's profile. In some embodiments, the mentee's profile includes the mentee's personal information, such as age and gender, the mentee's risk profile, the mentee's success odds and tags associated with the mentee, such as location tag (e.g., New York City), language tag (e.g. Spanish speaking) and behavior tag (e.g., aggressive behavior). The mentor's profile includes the mentor's personal information, the mentor's work history, and tags associated with the mentor, such as location tag (e.g., New York City), language tag (e.g. Spanish speaking) and experience tag (e.g., experience in handling aggressive behavior). The matching module may analyze the tags associated with the mentee's profile and the mentor's profile, and determine the best match based on a matching algorithm.

At block 310, the system 100 may track the success of each mentor-mentee relationship. The system 100 may track the success of the relationships as described above in reference to FIG. 2. After block 310 is complete, the method 300 may proceed to block 312.

At block 312, the system 100 may compensate the mentor based on how successful the mentor-mentee relationship is. The system 100 may gauge the success of the relationships as described above in reference to FIG. 2. After block 312 is complete (which may take years or even decades), the method 300 may end.

The above description is for the purpose of teaching the person of ordinary skill in the art how to practice the object of the present application, and it is not intended to detail all those obvious modifications and variations of it which will become apparent to the skilled worker upon reading the description. It is intended, however, that all such obvious modifications and variations be included within the scope of the present application, which is defined by the following claims. The aspects and embodiments are intended to cover the components and steps in any sequence which is effective to meet the objectives there intended, unless the context specifically indicates the contrary.

What is claimed is:

1. A method for providing mentoring service to at-risk people, comprising the steps of:
    (a) providing a system comprising:
        (1) one or more computing devices in data communication with each other, each device having at least one processor, a data communication connection, and one or more tangible non-transitory computer-readable media accessible by one or more computer processors, and
        (2) a plurality of databases, including a mentee database, a mentors' qualification database, a mentors' performance database, and a mentors' compensation database, wherein the mentee database, mentors' qualification database, mentors' performance database, and mentors' compensation database are each stored in the one or more tangible non-transitory computer-readable media;
    (b) receiving, via a user interface of an application executing on one or more computer processors, a personal profile concerning an at-risk subject, wherein the personal profile comprises personal data, a risk profile comprises a plurality of risk factors and a plurality of mentee matching tags;
    (c) assigning, via the one or more computer processors, a risk point value to each of the plurality of risk factors based on severity level of the subject's risk factors and a risk point matrix stored on a memory device accessible by the one or more computer processors, wherein the risk point matrix is determined by evaluating data reflecting risks of other subjects compared to their later successes or failures, and estimated lifetime costs to society, as stored in the mentee database;

(d) determining, via the one or more computer processors, a total risk point value of the at-risk subject via the one or more computer processors;

(e) accepting the at-risk subject as a mentee candidate, if the total risk point value satisfies a pre-determined threshold value;

(f) searching, via the one or more computer processors, the mentor candidate database, wherein the mentor candidate database comprises a plurality of mentor profiles, wherein each of the plurality of mentor profiles comprises personal data, mentoring experience and a plurality of mentor matching tags;

(g) assigning, via the one or more computer processors, at least one mentor candidate to the mentee candidate, thereby establishing a mentor-mentee relationship, wherein the at least one mentor candidate is selected based on a match between the mentee matching tags and the mentor matching tags, and wherein the match is performed using a matching algorithm;

(h) receiving, via the user interface of the application, the at-risk subject's progress report after the establishment of the mentor-mentee relationship;

(i) comparing, via the one or more computer processors, the at-risk subject's progress to at-risk individual success odds or ex-convict success odds stored in the mentee database accessible by the one or more computer processors;

(j) obtaining, via the one or more computer processors, (1) the at-risk subject's income tax records from relevant governmental agencies, (2) the at-risk subject's retirement plan contribution information, and/or education plan contribution information from relevant financial institutions;

(k) determining, via the one or more computer processors, a level of financial compensation to the mentor based on the at-risk subject's progress to at-risk individual success odds or ex-convict success odds stored on a memory device accessible by the one or more computer processors, the at-risk subject's income tax records, the at-risk subject's retirement plan contribution information and/or education plan contribution information, and expected lifetime costs to society;

(l) obtaining approval for the amount of financial compensation from an oversight board or governmental agency;

(m) transmitting a notice to a relevant governmental agency about the approved amount; and (n) financially compensating the mentor the approved amount in the form of an income tax credit or payment.

2. The method of claim 1, wherein the financial compensation is provided in the form of a payment to the mentor's retirement plan and/or education plan, wherein amount of the cash payment is calculated as a percentage of the at-risk subject's income tax payment(s), retirement plan contribution(s), and/or education plan contribution(s).

3. The method of claim 1, wherein the notice is subject to review and approval by the relevant governmental agency and wherein the relevant governmental agency issues a payment for the amount approved by the relevant governmental agency.

4. The method of claim 3, wherein said notice causes the relevant governmental agency to electronically deposit the approved amount into a bank account designated by the mentor.

5. The method of claim 1, wherein the financial compensation is provided in the form of (1) an income tax credit; (2) a contribution to mentor's retirement plan and/or (3) a contribution to mentor's education plan, and wherein said notice causes the relevant governmental agency to (1) issue a notification to the mentor of an income tax credit for the approved amount and electronically enter the income tax credit on the mentor's tax record, or (2) issue a notification to the mentor of a contribution to mentor's retirement plan and/or education plan for the approved amount and electronically transfer funds to the mentor's retirement plan and/or education plan.

6. The method of claim 5, wherein the notice is subject to review and approval by the relevant governmental agency and/or oversight board.

7. The method of claim 1, further comprising the steps of:
retrieving, via the one or more computer processors, information about how to reduce risks associated with one or more of the plurality of risk factors from a database stored on a memory device, and
electronically delivering, via the one or more computer processors, the information to the oversight board and/or a mentor approved by the oversight board.

8. The method of claim 1, further comprising the steps of:
retrieving, via the one or more computer processors, information about how to reduce risks associated with one or more of the plurality of risk factors from a database stored on a memory device, and
electronically delivering, via the one or more computer processors, an alert to the mentor over a wireless communication channel to a wireless device associated with the mentor, wherein the alert activates an application on the wireless device that causes the wireless device to connect, via Internet, to the one or more computer processors and download said information.

9. The method of claim 1, wherein the plurality of risk factors comprise one or more of the factors selected from the group consisting of age, gender, weight, height, job history, history of traffic violations, alcohol consumption, drug use history, personal medical history, academic performance in school, attendance history at school, appropriateness of behavior at school, extra-curricular activities, gang involvement, personality assessment, assessment of siblings and/or parents and/or guardians, probability of dropping out of school, probability of becoming pregnant, probability of committing a crime, probability of using illegal drugs, job history, probability of becoming habitually unemployed, and probability of returning to prison.

10. A networked computer system for providing mentoring service to at-risk people, comprising:
one or more computing devices in data communication with each other, each device having at least one processor, a data communication connection, and one or more tangible non-transitory computer-readable media accessible by one or more computer processors;
a plurality of databases, including a mentee database, a mentors' qualification database, a mentors' performance database, and a mentors' compensation database, wherein the mentee database, mentors' qualification database, mentors' performance database, and mentors' compensation database are each stored in the one or more tangible non-transitory computer-readable media; and
one or more tangible, non-transitory computer readable media accessible by the one or more computer processors, wherein the one or more tangible, non-transitory computer readable media comprise instructions that, when executed by the one or more computer processors, cause the one or more computer processors to perform:

(a) receiving, via a user interface of an application executing on the one or more computer processors, a risk profile concerning an at-risk subject, wherein the risk profile comprises a plurality of risk factors and their expected lifetime costs to society;

(b) assigning, via the one or more computer processors, a risk point value to each of the plurality of risk factors based on severity level of the subject's risk factors and their expected lifetime cost to society and a risk point matrix stored on a memory device accessible by the one or more computer processors, wherein the risk point matrix is determined by evaluating data reflecting risks of other subjects compared to their later successes or failures and expected lifetime costs to society, as stored in the mentee database;

(c) determining, via the one or more computer processors, a total risk point value of the at-risk subject via the one or more computer processors;

(d) accepting the at-risk subject as a mentee candidate, if the total risk point value satisfies a pre-determined threshold value;

(e) searching, via the one or more computer processors, the mentor candidate database, wherein the mentor candidate database comprises a plurality of mentor profiles, wherein each of the plurality of mentor profiles comprises personal data, mentoring experience and a plurality of mentor matching tags;

(f) assigning, via the one or more computer processors, at least one mentor candidate to the mentee candidate, thereby establishing a mentor-mentee relationship, wherein the at least one mentor candidate is selected based on a match between the mentee matching tags and the mentor matching tags, and wherein the match is performed using a matching algorithm;

(g) receiving, via the user interface of the application, the at-risk subject's progress report after the establishment of the mentor-mentee relationship;

(h) comparing, via the one or more computer processors, the at-risk subject's progress to the progress achieved by other at-risk individuals and their success odds or ex-convict progress and success odds stored in the mentee database accessible by the one or more computer processors;

(i) obtaining, via the one or more computer processors, (1) the at-risk subject's income tax records from relevant governmental agencies, and/or (2) the at-risk subject's retirement plan contribution information, and/or education plan contribution information from relevant financial institutions;

(j) determining, via the one or more computer processors, a level of financial compensation to the mentor based on the at-risk subject's progress to at-risk individual success odds or ex-convict success odds stored on a memory device accessible by the one or more computer processors, the at-risk subject's income tax records, the at-risk subject's retirement plan contribution information and/or education plan contribution information, and expected lifetime costs to society;

(k) obtaining approval for the amount of financial compensation from an oversight board or governmental agency;

(l) transmitting a notice to a relevant governmental agency about the approved amount; and (m) financially compensating the mentor the approved amount in the form of an income tax credit or payment.

11. The system of claim 10, wherein the financial compensation is provided in the form of a cash payment to the mentor, wherein amount of the cash payment is calculated as a percentage of (1) the at-risk subject's income tax payment(s), and/or (2) the at-risk subject's contribution(s) to the at-risk subject's retirement plan and/or education plan, and/or (3) the at-risk subject's avoidance of negative outcomes and events that results in costs to society.

12. The system of claim 10, wherein the notice is subject to review and approval by the relevant governmental agency and wherein the relevant governmental agency issues a payment for the amount approved by the relevant governmental agency.

13. The system of claim 12, wherein said notice causes the relevant governmental agency to electronically deposit the approved amount into a bank account designated by the mentor.

14. The system of claim 10, wherein the financial compensation is provided in the form of a contribution to mentor's retirement plan and/or education plan, and wherein said notice causes the relevant governmental agency to issue a notification to the mentor of a contribution to mentor's retirement plan and/or education plan for the approved amount and electronically transfer the contribution to mentor's retirement plan and/or education plan.

15. The system of claim 10, wherein the one or more tangible, non-transitory computer readable media comprise instructions that, when executed by the one or more processors, cause the one or more processors to perform the steps of:

retrieving, via the one or more computer processors, information about how to reduce risks associated with one or more of the plurality of risk factors from a database stored on a memory device, and electronically delivering, via the one or more computer processors, the information to the oversight board and/or a mentor approved by the oversight board and/or the mentee's parents or guardians.

16. The system of claim 15, wherein the information is delivered over a wireless communication channel to a wireless device associated with the mentor.

17. The system of claim 16, wherein the one or more tangible, non-transitory computer readable media comprise instructions that, when executed by the one or more processors, cause the one or more processors to perform the steps of:

retrieving, via the one or more computer processors, information about how to reduce risks associated with one or more of the plurality of risk factors from a database stored on a memory device, and electronically delivering, via the one or more computer processors, an alert to the mentor over a wireless communication channel to a wireless device associated with the mentor, wherein the alert activates an application on the wireless device that causes the wireless device to connect, via Internet, to the one or more computer processors and download said information.

18. A tangible computer readable medium, comprising instructions that, when executed by a computer processor, cause the processor to perform:

receiving, via a user interface on a computer, a risk profile concerning an at-risk subject, wherein the risk profile comprises a plurality of risk factors;

assigning, via a computer processor, a risk point value to each of the plurality of risk factors based on severity level of the subject's risk factors and a risk point matrix stored on a memory device accessible by the computer processor, wherein the risk point matrix is determined by evaluating data reflecting risks of other subjects compared to their later successes or failures and estimated lifetime cost to society, as stored in a mentee database;

determining, via the computer processor, a total risk point value of the at-risk subject via the one or more computer processors;

accepting the at-risk subject as a mentee candidate, if the total risk point value satisfies a pre-determined threshold value;

searching, via the computer processor, a mentor candidate database, wherein the mentor candidate database comprises a plurality of mentor profiles, wherein each of the plurality of mentor profiles comprises personal data, mentoring experience and a plurality of mentor matching tags;

assigning, via the computer processor, at least one mentor candidate to the mentee candidate, thereby establishing a mentor-mentee relationship, wherein the at least one mentor candidate is selected based on a match between the mentee matching tags and the mentor matching tags, and wherein the match is performed using a matching algorithm;

receiving, via the user interface of the application, the at-risk subject's progress report after the establishment of the mentor-mentee relationship;

comparing, via the computer processor, the at-risk subject's progress to at-risk individual success odds or ex-convict success odds stored in the mentee database accessible by the computer processor;

obtaining, via the computer processor, (1) the at-risk subject's income tax records from relevant governmental agencies, and/or (2) the at-risk subject's retirement plan contribution information, and/or education plan contribution information from relevant financial institutions;

determining, via the one or more computer processors, a level of financial compensation to the mentor based on the at-risk subject's progress to at-risk individual success odds or ex-convict success odds stored on a memory device accessible by the one or more computer processors, the at-risk subject's income tax records, the at-risk subject's retirement plan contribution information and/or education plan contribution information, and expected lifetime costs to society;

obtaining approval for the amount of financial compensation from an oversight board or governmental agency;

transmitting a notice to a relevant governmental agencies about the approved amount; and financially compensating the mentor the approved amount in the form of an income tax credit or payment, wherein the approved amount of the income tax credit or payment is calculated as a percentage of the at-risk subject's income tax payment, the at-risk subject's retirement plan contribution information and/or education plan contribution each year, or reflects an income tax credit or payment based on the mentee's achievement of one or more milestones or avoidance of events that results in costs to society, and wherein said notice causes the relevant governmental agency to issue a payment for the approved amount.

19. The tangible computer readable medium of claim 18, wherein the financial incentive is provided in the form of an income tax credit for the mentor or a contribution to the mentor's retirement plan and/or education plan, and wherein said notice causes the relevant governmental agency to issue a notification to the mentor of the income tax credit, or the contribution to the mentor's retirement plan and/or education plan, for the approved amount and electronically enter the income tax credit on the mentor's tax record or electronically transfer the contribution to the mentor's retirement plan and/or education plan.

20. The tangible computer readable medium of claim 18, further comprising instructions that, when executed by the computer processor, cause the computer processor to perform the step of:

retrieving, via the one or more computer processors, information about how to reduce risks associated with one or more of the plurality of risk factors from a database stored on a memory device, and electronically delivering, via the computer processor, an alert to the mentor over a wireless communication channel to a wireless device associated with the mentor, wherein the alert activates an application on the wireless device that causes the wireless device to connect, via Internet, to the computer processor and download said information.

* * * * *